(12) United States Patent
Shah (10) Patent No.: US 10,154,963 B2
(45) Date of Patent: Dec. 18, 2018

(54) CONTROLLED-RELEASE FORMULATIONS COMPRISING TORSEMIDE

(71) Applicant: Sarfez Pharmaceuticals, Inc., Vienna, VA (US)

(72) Inventor: Salim Shah, Vienna, VA (US)

(73) Assignee: SARFEZ PHARMACEUTICALS, INC., Vienna, VA (US)

( * ) Notice: Subject to any disclaimer, the term of this patent is extended or adjusted under 35 U.S.C. 154(b) by 0 days.

(21) Appl. No.: 15/027,355

(22) PCT Filed: Dec. 26, 2013

(86) PCT No.: PCT/US2013/077732
§ 371 (c)(1),
(2) Date: Apr. 5, 2016

(87) PCT Pub. No.: WO2015/050570
PCT Pub. Date: Apr. 9, 2015

(65) Prior Publication Data
US 2016/0243042 A1    Aug. 25, 2016

Related U.S. Application Data

(60) Provisional application No. 61/887,396, filed on Oct. 6, 2013.

(51) Int. Cl.
*A61K 9/20* (2006.01)
*A61K 45/06* (2006.01)
(Continued)

(52) U.S. Cl.
CPC .............. *A61K 9/2054* (2013.01); *A61K 9/20* (2013.01); *A61K 9/2031* (2013.01); *A61K 31/44* (2013.01); *A61K 31/64* (2013.01); *A61K 45/06* (2013.01)

(58) Field of Classification Search
None
See application file for complete search history.

(56) References Cited

U.S. PATENT DOCUMENTS 5,895,663 A * 4/1999 Irwin .................. A61K 9/2054
424/465
2002/0156124 A1  10/2002 Gao et al.
(Continued)

FOREIGN PATENT DOCUMENTS

| CN | 1919197 A | 2/2007 |
| WO | WO-2005/092291 A1 | 10/2005 |
| WO | WO 2007/086078 A2 | 8/2007 |

OTHER PUBLICATIONS

Lant, Evolution of diuretics and ACE inhibitors, their renal and antihypertensive actions, parallels and contrasts, Br.J.Clin Pharmac (1987), 23,27S-41S).*
(Continued)

*Primary Examiner* — Robert A Wax
*Assistant Examiner* — Melissa S Mercier
(74) *Attorney, Agent, or Firm* — S&L US IP Attorneys, P.C.; Eric Brandon Lovell; Timothy Marc Shropshire (57) ABSTRACT

Disclosed herein are controlled-release (GR, e.g., extended-release (ER) or prolonged-release (PR)) oral dosage formulation comprising an effective amount of Torsemide or a pharmaceutically acceptable salt thereof and at least one sustained release excipient comprising a polymer, wherein the at least one matrix component is selected from the group consisting of: hydroxy propyl cellulose (HPC), hydroxypropyl methyl cellulose (HPMC), glyceryl behenate, and a polyethylene glycol glyceride. Torsemide may be present in the formulation in a range of about 1 wt % to about 20 wt %, or about 5 wt % to about 10 wt % and the matrix component is present in the formulation in a range of about 5 wt % to about 50 wt %, or about 15 wt % to about 35 wt
(Continued)

%. The formulation may further comprise at least one binder, lactose, talc and magnesium stearate. Methods of making and using the controlled-release oral dosage Torsemide formulation are also disclosed. A novel mechanism for Torsemide action in diuresis is further disclosed.

9 Claims, 6 Drawing Sheets

(51) Int. Cl.
*A61K 31/64* (2006.01)
*A61K 31/44* (2006.01)

(56) References Cited

U.S. PATENT DOCUMENTS

| | | |
|---|---|---|
| 2003/0119882 A1 | 6/2003 | Maegerlein |
| 2003/0152622 A1 | 8/2003 | Louie-Helm et al. |
| 2005/0169991 A1* | 8/2005 | Sanghvi ............... A61K 9/2009 |
| | | 424/468 |
| 2007/0104778 A1 | 5/2007 | Zeng et al. |
| 2007/0196482 A1 | 8/2007 | Sanghvi et al. |
| 2008/0187585 A1* | 8/2008 | Romero ............... A61K 31/64 |
| | | 424/465 |

OTHER PUBLICATIONS

Williams et al. (Investigation of Excipient Type and Level on Drug Release from Controlled Release tablets containing HPMC, Pharmaceutical Development and Technology, 7(2), 181-193 (2002).*
Dow (Using METHOCEL cellulose ethers for controlled release of drugs in hydrophilic matrix systems (accessed online Feb. 8, 2017).*
Aurora-Pharma, Product Catalogue, Microcrystalline Cellulose Vivapur, Heweten, Emcocel, Available online May 10, 2012).*
International Search Report dated May 1, 2014 in PCT/US2013/077732 (1 pg.).
International Preliminary Report on Patentability dated Oct. 23, 2015 in PCT/US2013/077732 and Article 34 Amendments to the claims as filed on Apr. 30, 2015 (12 pgs.).
Extended European Search Report dated Jun. 14, 2017 in related EP Appl. No. 13 89 5004 (8 pgs.).

* cited by examiner

CONTROLLED-RELEASE FORMULATIONS COMPRISING TORSEMIDE

FIELD OF THE INVENTION

The invention is directed to controlled-release (CR, e.g., extended-release (ER) or prolonged-release (PR)) oral dosage formulation comprising an effective amount of Torsemide or a pharmaceutically acceptable salt thereof and at least one controlled-release excipient.

BACKGROUND OF THE INVENTION

Congestive heart failure (CHF) affects 1.7% of the US population, 4.6 million people have chronic heart failure, there are 550,000 new cases per annum and approximately 60% are over 70 years of age. The etiological causative factors are coronary heart disease, hypertension, cardiac valvular disease, arrhythmias, cardiomyopathy and diabetes. It is associated with high mortality. In the US the median survival following onset of CHF is 1.7 years in men and 3.2 years in women. Data generated from Scotland shows a 3-year mortality rate after first hospitalization for CHF patients' age 65 years and older is approximately 66%.

Diuretics play an essential role in modern cardiovascular therapy, and are currently recommended for the treatment of CHF. Diuretics suffer from many defects or complications including electrolyte and metabolic disturbances and reduction in glomerular filtration rate (GFR). The GFR is already reduced in most patients with edematous conditions and declines further over time eventually mandating the use of loop diuretics since these agents have the most potent acute pharmacological action of natriuresis and diuresis. However, any further fall in GFR will compromise the fluid and salt depleting actions of the diuretic and may lead to a "cardio-renal syndrome." Prior studies with furosemide in normal subjects consuming a high salt intake showed that furosemide increased the GFR immediately after the dose, but reduced it thereafter by circa 23% during the remainder of the day.

Despite their unrivaled acute effectiveness, loop diuretics have been disappointing therapeutic agents. They cause little or no reduction in blood pressure (BP) in hypertensives, resulting in a preference for less acutely natriuretic and diuretic drugs such as thiazides or mineralocorticosteroid antagonists (MRAs). Furosemide's short half-life and extreme variation in bioavailability may account for its unpredictable effects in treating patients with CHF and bumedtanide is even more short acting.

A class defect of loop diuretics is their short duration of action of 2-4 hours even after oral dosing. Two problems may ensue. First, the plasma concentration of the loop diuretic resides within the "most efficient" 25% to 75% of maximum level for less than one hour. Second, their abrupt action leaves about 20 hours for the kidney to regain the salt and water lost before the next daily dose. This accounted for the failure of furosemides or bumetanide to cause net $Na^+$ loss over 1-3 days of once daily administration to normal subjects unless dietary salt was restricted.

Torsemide has been developed as a newer type of loop diuretic with a longer half-life, longer duration of action, and higher bioavailability compared to the most commonly used loop diuretic, furosemide.

Torsemide is routinely used for the treatment of both acute and chronic CHF and arterial hypertension (AH). Torsemide is similar to other loop diuretics in terms of its mechanism of diuretic action. It has higher bioavailability (about 80%) and a longer elimination half-life (3 to 4 hours) than furosemide. In the treatment of CHF Torsemide (5 to 20 mg/day) has been shown to be an effective diuretic. Non-diuretic dosages (2.5 to 5 mg/day) of Torsemide have been used to treat essential AH, both as monotherapy and in combination with other antihypertensive agents (e.g. calcium channel blocker, ACE inhibitors, ARBs, diuretics, and alpha and/or beta blockers). When used in these dosages, Torsemide lowers diastolic blood pressure to below 90 mm Hg in 70 to 80% of patients. Antihypertensive efficacy of Torsemide is similar to that of thiazides and related compounds. Thus low-dose Torsemide constitutes an alternative to thiazides diuretics in the treatment of essential AH.

Torsemide also appears to have additional actions beyond a pure diuretic effect, such as an anti-aldosterone effect and vaso-relaxation effect. These effects of Torsemide are mediated via several biological pathways including but not limited to modulation of renin-angiotensin-aldosterone system (RAAS), modulation of guanylyl cyclase activity, modulation of secretion of brain natriuretic peptide and atrial natriuretic factor, modulation of mineralocorticoid receptors, collagen/collagen type I, and myocardial fibrosis. All of these effects of Torsemide are dependent and concentration and duration of Torsemide bioavailability. The extended release Torsemide formulations described here maintain Torsemide bioavailability for longer duration as compared to the immediate release Torsemide and thereby differentially modulate above biological pathways. Moreover, studies have also investigated whether the superior pharmacokinetics and pharmacological activity of Torsemide result in a favorable clinical outcome. Their results have indicated that, in comparison with furosemide, Torsemide improves left ventricular function, reduces mortality as well as the frequency and duration of heart failure-related hospitalization, and improves quality of life, exercise tolerance and NYHA functional class in patients with congestive heart failure. Thus, Torsemide appears to be a promising loop diuretic that contributes to better management of patients with heart failure.

Torsemide is a high-ceiling loop diuretic, which acts on the thick ascending limb of the loop of Henle to promote rapid and marked excretion of water, sodium and chloride. Like furosemide, its major site of action is from the luminal side of the cell. Torsemide is at least twice as potent as furosemide on a weight-for-weight basis, produces equivalent diuresis and natriuresis at lower urinary concentrations and has a longer duration of action, allowing once-daily administration without the paradoxical antidiuresis seen with furosemide. Torsemide also appears to promote excretion of potassium and calcium to a lesser extent than furosemide. In trials of up to 48 weeks duration in patients with mild to moderate essential hypertension, Torsemide, administered as a single daily dose, has been shown to achieve adequate blood pressure control reaching steady-state within 8 to 12 weeks. Those patients not responding initially have generally responded to a doubling of the dose. Comparative trials of up to 6 months show Torsemide is as effective as indapamide, hydrochlorothiazide or a combination of triamterene/hydrochlorothiazide in maintaining control of blood pressure. Torsemide has also been used successfully to treat oedematous states associated with chronic congestive heart failure, renal disease and hepatic cirrhosis. In short term trials control of blood pressure, bodyweight and residual edema has been sustained. Torsemide appears to be a useful alternative to furosemide in these patients, providing potent and long-lasting diuresis while being relatively potassium and calcium sparing. In clinical trials to date Torsemide has been well tolerated with adverse effects of a mild, transient nature reported by only small numbers of patients. Changes in biochemical parameters have been common, including decreases in plasma sodium and potassium levels and increases in plasma creatinine and uric acid levels. These changes are typical of loop diuretics. No changes were clinically significant nor were clinically relevant changes noted in glucose metabolism, cholesterol or triglyceride levels or in haematological values. Thus, Torsemide is an interesting new loop diuretic with potential use in the treatment of mild to moderate essential hypertension and of oedematous states in which diuretic therapy is warranted. Preliminary studies suggest it to be as efficacious as other diuretics in common use and to have some advantage over furosemide in duration of action and in effects on potassium and calcium.

CHF is the cause of significant mortality all over the world and its incidence and prevalence are increasing. Fluid retention and volume overload are responsible in large part of morbidity related to heart failure. Torsemide is the only loop diuretic for which it has been shown to effectively lower high blood pressure even with low doses. In addition, Torsemide is a very safe drug. In a postmarketing surveillance study (TORIC) of 1,377 patients with CHF, Torsemide significantly reduced cardiovascular mortality in comparison to furosemide; see Ishido et al., Torsemide for the treatment of heart failure. *Cardiovasc. Hematol. Disord. Drug Targets.* 2008 June; 8(2):127-32. Review, herein incorporated by reference in its entirety. In a recent study, Torsemide reversed myocardial fibrosis and reduced collagen type I synthesis, improving cardiac remodeling in patients with CHF; see Preobrazhenskii et al., Torsemide is the effective loop diuretic for long-term therapy of arterial hypertension. *Kardiologiia.* 2011; 51(4):67-73. Review, herein incorporated by reference in its entirety.

More than 20 million people in the U.S. have Chronic Kidney Disease (CKD). Over half a million people are treated annually for End-Stage Renal Disease (ESRD). In patients with advanced renal failure, high doses of loop diuretics are required to promote negative sodium and water balance and to treat hypertension. Torsemide is a new loop diuretic that has a high bioavailability of 80% and a plasma half-life of 3-5 hours, which remains unchanged in chronic renal failure. Even in patients with advanced renal failure, intravenous and oral high-dose Torsemide proves effective in increasing fluid and sodium excretion in a dose-dependent manner. A number of studies in renal failure patients provide evidence that, on a weight-by-weight basis, the ratio of diuretic potency between Torsemide and furosemide is 1:2.5 after oral dosing and 1:1 after intravenous administration.

However, common problems with diuretics are acute and chronic tolerance. Acute tolerance occurs in a breaking phenomenon associated with a shift to the right of the dose response curve and occurs after initial dosing. Chronic tolerance occurs after 5-10 weeks of dosing and is associated with tubular hypertrophy and sodium rebound phenomena. Although multiple physiological mechanisms are involved in this phenomenon, acute volume depletion is the main stimulus to this phenomenon.

Oral controlled-release controlled-release (CR, e.g., extended-release (ER) or prolonged-release (PR)) formulations overcome many of the drawbacks of conventional immediate release (IR) dosage forms.

Figure 1:
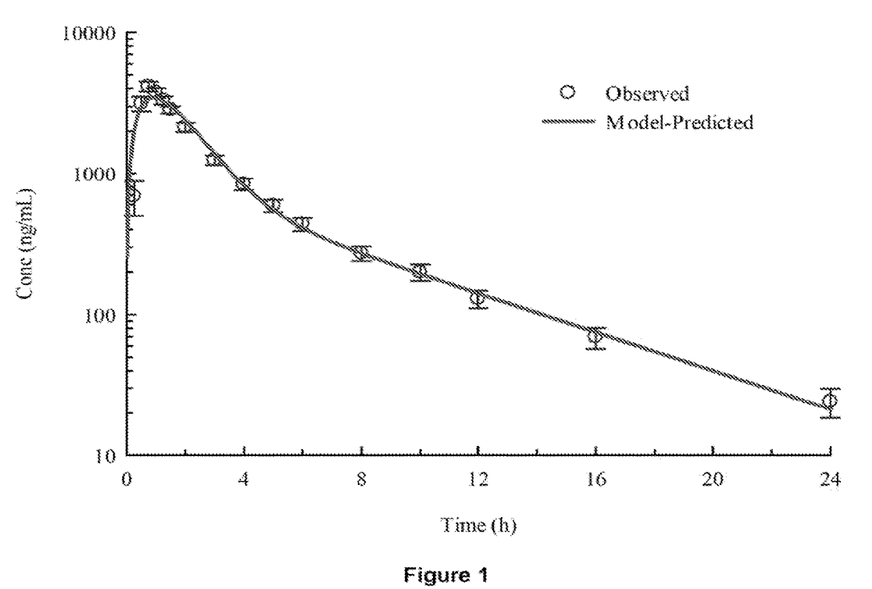
FIG. 1 shows observed (mean±standard error) and model-predicted Torsemide plasma concentrations after administration of a 20 mg IR formulation.

For example, FIG. 1 shows observed and model-predicted plasma concentration of Torsemide after administration of a 20 mg immediate-release (IR) formulation. As can be seen, the plasma concentration peaks within 1 hour of administration and the concentration decreases thereafter. This may lead to alternating periods of toxic levels and sub-therapeutic concentrations, and thereby decreasing the therapeutic efficacy and inviting toxic side effects.

Contrary to IR dosage forms, CR tablets are not associated with alternating periods of toxic levels and sub-therapeutic concentrations, and thereby improving the therapeutic efficacy and avoiding toxic side effects. Therefore, CR has certain distinct advantages such as (1) reduction in drug plasma level fluctuation with maintenance of a steady plasma level of the drug over a prolonged time period, ideally simulating an intravenous infusion of a drug; (2) reduction in adverse side effects and improvement in tolerability, as drug plasma levels are maintained with in a narrow window with no sharp peaks and with AUC of plasma concentration versus time curve comparable with total AUC from multiple dosing with immediate release dosage forms; (3) patient comfort and compliance, as oral drug delivery is the most common and convenient for patients, and a reduction in dosing frequency enhances compliance; (4) reduction in healthcare cost, as the total cost of therapy of the controlled release product could be comparable or lower than the immediate release product. With reduction in side effects, the overall expense in disease management also would be reduced, this greatly reduces the possibility of side effects, as the scale of side effects increase as we approach the maximum safe concentration; and (5) avoid night time dosing, as it is also good for patients to avoid the dosing at night time.

Controlled release products can be classified as follows: (1) reservoir systems including enteric coated products; (2) osmotic systems; (3) ion-exchange resins; and (4) matrix systems. Matrix systems can further be subdivided into (a) monolithic matrix tablets; (b) erodible (hydrophobic) matrix tablets; and (c) gel forming hydrophilic matric tablets Most monolithic matrix tablets use inert matrix, which does not interact (inert) with biological fluids. The main reason for popularity of this system is drug release from the matrix is independent of the states and condition of digestive juices, which shows quite large inter- and intra-patients variability. Nowadays, research in this area focuses on natural biopolymers such as cellulose and starch derivatives, some of which could be considered semi-inert (e.g. ethylcellulose).

Gel-forming hydrophilic or swellable matrix systems are homogeneous or heterogeneous systems in which the drug is dispersed in a swellable hydrophilic polymer. The drug release is a function of polymer characteristics. Most widely studies gel-forming polymer in controlled release is poly (hydroxyethyl methacrylate (pHEMA). Because of their swelling capacity, several cellulose derivatives are applied as swelling gel-forming controlled release drug delivery excipients and most widely used is hydroxypropylmethylcellulose (HPMC). However, a variety of different molecular weight HPMC are available and they varies in their release characteristics. Specifically, viscosity and erosion/dissolution characteristic of gel layer varies greatly and allows manipulations with expected drug released profile.

Other swellable polymers used in matrix tablets are natural or artificial gum, and dextrans.

Erodible polymers such as polyanhydrides provide for other types of excipients for controlled release drug with zero-order profile.

U.S. Patent Publication No. 2003/0152622 A1, herein incorporated by reference in its entirety, describes formulations of an erodible gastric retentive oral diuretic, and exemplifies furosemide as the diuretic.

U.S. Patent Publication No. 2007/0196482 A1, herein incorporated by reference in its entirety, describes a sustained release oral dosage form using gum-based gelling gum such as xanthan and locust bean gums.

Moreover, a group in Spain has developed a prolonged-release (PR) Torsemide; see Diez et al., TORAFIC study protocol: Torsemide prolonged release versus furosemide in patients with chronic heart failure. *Expert Rev Cardiovasc Ther.* 2009 August; 7(8):897-904, herein incorporated by reference in its entirety.

Biologically, PR Torsemide was found to be similar in systemic exposure but significantly slower rates of absorption and lower fluctuations in plasma concentrations. Its natriuretic efficiency is higher and diuresis is more constant, with a better tolerability.

However, both the controlled release drug claimed in 2003/0152622-A1 and 2007/0196482-A1 applications, both herein incorporated by reference in their entireties, failed to achieve desired effect sin clinical developments. Additionally, the Spanish version of PR Torsemide shows only a modest release profile of about 5-6 hours.

Therefore, in view of the above, there exists a need in the art for improving the effectiveness of diuretic therapy via better-sustained (e.g., extended) release loop diuretic such as Torsemide.

SUMMARY OF THE INVENTION

In an aspect, the invention provides an extended-release oral dosage formulation, such as a tablet, comprising a therapeutically effective amount of Torsemide or a pharmaceutically acceptable salt thereof and at least one matrix component, wherein the at least one matrix component is selected from the group consisting of: hydroxy propyl cellulose (HPC), hydroxpropyl methyl cellulose (HPMC), glyceryl behenate, and a polyethylene glycol glyceride. In an aspect, Torsemide is present in the formulation in a range of about 1 wt % to about 20 wt %, or about 5 wt % to about 10 wt % and the matrix component is present in the formulation in a range of about 5 wt % to about 50 wt %, or about 15 wt % to about 35 wt %.

In an aspect, the extended-release oral dosage formulation may comprise about 5 wt % to about 10 wt % of Torsemide or a pharmaceutically acceptable salt thereof; about 10 wt % to about 40 wt % of a matrix component; about 50 wt % to about 60 wt % of at least one binder; about 5 wt % to about 15 wt % of lactose; about 1 wt % to about 3 wt % of talc; and about 0.5 wt % to about 1 wt % of magnesium stearate.

In another aspect, an extended-release oral dosage formulation may further comprise at least one binder, lactose, talc and magnesium stearate is provided, wherein the at least one binder present is a microcrystalline cellulose binder and is present in the formulation in a range of about 25 wt % to about 75 wt %, lactose is present in the formulation in a range of about 1 wt % to about 20 wt %, talc is present in the formulation in a range of about 1 wt % to about 5 wt %, and magnesium stearate is present in the formulation in a range of about 0.1 wt % to about 2 wt %.

In yet another aspect, the extended-release oral dosage formulation may be combined with and/or comprise at least one of an ACE inhibitor, an aldosterone receptor antagonist, a calcium channel blocker, a thiazide diuretic, an angiotensin receptor blocker, an alpha blocker, potassium-sparing diuretic (e.g. Amiloride), central sympathetic suppressant (e.g. Moxonidine, Rilmenidine, Clonidine), and a beta-blocker, the ACE inhibitor is selected from the group consisting of: alacepril, benazepril, captopril, cilazapril, delapril, enalapril, enalaprilat, fosinopril, fosinoprilat, imidapril, lisinopril, perindopril, quinapril, ramipril saralasin acetate, temocapril, trandolapril, ceranapril, moexipril, quinaprilat and spirapril.

In yet another aspect, a method of making an extended-release oral dosage formulation comprising Torsemide may comprise forming a mixture comprising at least Torsemide and a matrix component; wet granulating the mixture to form particles; sizing the particles; and forming the extended-release oral dosage formulation.

In a further aspect, a method of using the extended-release oral dosage formulation comprising Torsemide may comprise administering a therapeutically effective amount of the formulation to a subject in need thereof. In a further aspect, a method of mitigating the reduction of an amount of GFR and/or increasing an amount of GFR may comprise administration of a therapeutically effective amount of the Torsemide ER formulations described herein to a patient in need thereof. In a further aspect, a method of increasing fluid and/or $Na^+$ loss may comprise administration of a therapeutically effective amount of the Torsemide ER formulations described herein to a patient in need thereof.

In yet a further aspect, administration of the extended-release oral dosage formulation comprising Torsemide leads to a novel mechanism for Torsemide action in diuresis by acting on $Na^+/K^+/2Cl^-$ co-transporter in the kidney and/or acting on guanylate cyclase (GC), specifically membrane bound GC and modulated actions of peptide hormones such as brain natriuretic peptide (BNP) and atrial natriuretic peptide.

BRIEF DESCRIPTION OF THE FIGURES

FIG. 6A shows urine flow; FIG. 6B shows creatinine clearance; FIG. 6C shows sodium excretion; FIG. 6D shows potassium excretion. The mean values for the previous 24 hours are indicated by the horizontal dotted lines.

DETAILED DESCRIPTION OF THE INVENTION

The present invention now will be described more fully hereinafter with reference to the accompanying figures, in which embodiments of the invention are shown. This invention may, however, be embodied in many alternate forms and should not be construed as limited to the embodiments set forth herein.

Modeling studies have shown that ER Torsemide may provide an improved diuretic therapy over IR Torsemide, particularly using a controlled-release loop diuretic. The molecular structure of Torsemide is shown below.

ER formulations comprising Torsemide may comprise, as a controlled-release agent, a matrix based on erosion-controlled polymers and/or a matrix based on lipids and fatty acids.

Erosion Controlled Polymer Based Matrix Tablet Formulations

Matrix technologies based on hydrophilic polymers have proven popular among the oral controlled drug delivery technologies because of their simplicity, ease in manufacturing, high level of reproducibility, stability of raw materials and dosage forms, ease of scale-up and process validation. Due to these advantages, the matrix tablet platform may be used for Torsemide ER formulations.

Polymers with varying chemistry/molecular weights, for example Hydroxy Propyl Cellulose (HPC), Hydroxypropyl methyl cellulose (HPMC) may be used so as to target the drug release from the matrix independent of pH. Torsemide may be mixed with polymers and other excipients, this mixture may then be wet granulated, dried and sized, then compressed into tablet form. The polymer may be added into the formulation in the concentration between about 5% and about 50% based on the total tablet weight, preferably between about 10% and about 40%, and more preferably between about 15% and about 35% based on the total tablet weight. If required, pore formers may be added into the formulation to facilitate drug diffusion from the matrix. Since the solubility of Torsemide is low in water, medium and low molecular weight polymers may be used for granulation.

Lipid and Fatty Acid Based Tablet Formulations

Lipid excipients may be utilized to deliver clinically relevant sustained drug release profiles (8, 12, 24 hours) through the creation of an insoluble matrix structure from which diffusion is the principal drug extended-release mechanism.

Many lipid and fatty acid based excipients may be used as a release controlling agent. A few of the excipients such as glyceryl behenate (e.g., Compritol) and polyethylene glycol glyceride (e.g., Gelucire) may be used for the development of ER tablets. These lipid excipients produce ER release tablet matrices with pH independent release kinetics. These tablets may be made using simple techniques that yield highly stable drug release profiles. Drug release profile may be modulated by the addition of hydrophilic diluents like lactose or water-insoluble diluents depending on the desired kinetics and tablet characteristics. A target profile as described in Table 1 may be used as reference.

TABLE 1

Target Profile Release Percentage.

| Time in Hr | Target Profile Torsemide Release in % |
|---|---|
| 1 Hr | 15-21 |
| 4 Hr | 50-65 |
| 8 Hr | 65-75 |
| 12 Hr | 80-95 |

The oral dosage ER Torsemide formulation may comprise Torsemide in a range of about 1 wt % to about 20 wt %. More preferably, the Torsemide may be present in a range of about 5 wt % to about 10 wt %. Most preferably, the Torsemide may be present in a range of about 6 wt % to about 7 wt %. Alternatively, the oral dosage ER Torsemide formulation may comprise Torsemide in a range of about 5 mg to about 50 mg. More preferably, the Torsemide may be present in a range of about 10 mg to about 40 mg or about 20 mg to about 30 mg. Most preferably, the formulation comprises 20 mg of Torsemide.

The matrix component (e.g., erosion-controlled polymer and/or lipid/fatty acid) may be comprised in the oral dosage formulation in a range of about 1 wt % to about 50 wt %. More preferably, the matrix component may be present in a range of about 10 wt % to about 40 wt %. Most preferably, the matrix component may be present in a range of about 15 wt % to about 35 wt %. Alternatively, the oral dosage ER Torsemide formulation may comprise the matrix component in a range of about 10 mg to about 90 mg. More preferably, the matrix component may be present in a range of about 20 mg to about 70 mg or about 30 mg to about 50 mg.

The ER oral dosage formulations may also comprise other ingredients, such as a binder or binders, lactose, talc and magnesium stearate.

The binder may be comprised in the oral dosage formulation as a single binder or a plurality of binders, for example a primary binder (e.g., by wt %) and a secondary binder, or binders. The primary binder may be a cellulose binder, and is preferably a microcrystalline cellulose binder such as Avicel PH 302, Avicel PH 101 and/or Avicel PH 102. The primary binder may be present in the oral dosage ER formulation in a range of about 25 wt % to about 75 wt %. More preferably, the primary binder may be present in a range of about 50 wt % to about 60 wt %. Most preferably, the primary binder may be present in a range of about 50 wt % to about 57 wt %. Alternatively, the oral dosage ER Torsemide formulation may comprise the primary binder in a range of about 50 mg to about 200 mg. More preferably, the primary binder may be present in a range of about 60 mg to about 150 mg or about 80 mg to about 100 mg.

Secondary binders, such as a polyvinylpyrrolidone (e.g., PVP K 30), may also be included in smaller wt % ranges, such as about 1 wt % to about 10 wt %, or more preferably 3 wt % to about 9 wt %. Alternatively, the oral dosage ER Torsemide formulation may comprise the secondary binder in a range of about 1 mg to about 20 mg. More preferably, the secondary binder may be present in a range of about 5 mg to about 15 mg.

Lactose may be present in the oral dosage ER formulation in a range of about 1 wt % to about 20 wt %. More preferably, lactose may be present in a range of about 5 wt % to about 15 wt %. Most preferably, lactose may be present in a range of about 8 wt % to about 14 wt %. Alternatively, the oral dosage ER Torsemide formulation may comprise lactose in a range of about 5 mg to about 50 mg. More preferably, lactose may be present in a range of about 10 mg to about 25 mg.

Talc and magnesium stearate may be present in the oral dosage ER formulation. Talc may be present in a range of about 1 wt % to about 5 wt %. More preferably, talc may be present in a range of about 1 wt % to about 3 wt %. Alternatively, the oral dosage ER Torsemide formulation may comprise talc in a range of about 1 mg to about 10 mg. More preferably, talc may be present in a range of about 2 mg to about 5 mg.

Magnesium stearate may be present in a range of about 0.1 wt % to about 2 wt %. More preferably, magnesium stearate may be present in a range of about 0.5 wt % to about 1 wt %. Alternatively, the oral dosage ER Torsemide formulation may comprise magnesium stearate in a range of about 0.5 mg to about 5 mg. More preferably, magnesium stearate may be present in a range of about 1 mg to about 2 mg.

The ER oral dosage Torsemide formulation may be used alone or in combination with other therapeutic agents such as, without limitation, ACE inhibitors, calcium channel blockers such as amlodipine, thiazide diuretics, angiotensin receptor blockers (ARBs) and alpha and beta-blockers. The other therapeutic agents may be administered with the ER Torsemide either sequentially or simultaneously. If administered simultaneously, a single capsule having a fixed ratio of the active agents may be used. If administered sequentially, the active agents may be used in multiple, separate capsules.

A combination therapy may comprise three active agents, such as an ACE inhibitor, an aldosterone receptor antagonist and a loop diuretic. For the ACE inhibitor and a loop diuretic combination, the formulations may comprise a weight ratio range from about 0.5% to about 1% based on the total tablet weight. These same agents may be present in the formulations in ratios of about 20:1 of the ACE inhibitor to the loop diuretic.

Examples of ACE inhibitor, which may be used in the combination therapy, may be selected from the group consisting of: alacepril, benazepril, captopril, cilazapril, delapril, enalapril, enalaprilat, fosinopril, fosinoprilat, imidapril, lisinopril, perindopril, quinapril, ramipril saralasin acetate, temocapril, trandolapril, ceranapril, moexipril, quinaprilat and spirapril.

Methods of making the ER oral dosage Torsemide formulations described herein are not particularly limited and may comprise: forming a mixture comprising Torsemide, a matrix component and other ingredients, granulating (e.g., wet granulating) the mixture to form particles, drying the particles, sizing the particles and forming an oral dosage controlled-release formulation, such as a tablet.

Methods of using the ER oral dosage Torsemide formulations described herein to treat the aforementioned conditions and diseases are also not particularly limited and may comprise administering a therapeutically effective amount of Torsemide to a subject in need thereof.

In-Vitro Studies

Example 1

In-vitro studies using Torsemide ER formulations were carried out and several ER formulations were used, including those based on an erosion-controlled, polymer-based matrix and a lipid/fatty acid based matrix.

For erosion-controlled, polymer-based matrix tablet formulations, Hydroxy Propyl Cellulose (HPC) was used as a controlled-release agent. Details of the release profile obtained from in-vitro stability studies are shown in Table 2 below.

TABLE 2

Release Profiles for ER Torsemide using HPC.

| S. No. | Ingredients (mg) | B. No. 11-173-01 | B. No. 11-173-03 | B. No. 11-173-04 | B. No. 11-173-05 | B. No. 11-173-07 |
|---|---|---|---|---|---|---|
| 1 | Torsemide | 10 | 10 | 10 | 10 | 10 |
| 2 | Avicel PH 302 | 84 | 98 | 100 | 91 | 92 |
| 3 | HPC HXF PH | 51 | 50 | 47 | 50 | 45 |
| 4 | Lactose (Super Tab) | — | 14 | 15 | 21 | 25 |
| 5 | Talc | 4 | 2 | 2 | 2 | 2 |
| 6 | Mag-Stearate | 1 | 1 | 1 | 1 | 1 |
|  |  | 150 | 175 | 175 | 175 | 175 |

Details of in-vitro dissolution testing results are shown in Table 3 below.

TABLE 3

In-Vitro Dissolution Testing Results

| Time in Hr | Target Release Profile | B. No. 11-173-01 | B. No. 11-173-03 | B. No. 11-173-04 | B. No. 11-173-05 | B. No. 11-173-07 |
|---|---|---|---|---|---|---|
| 1 hr | 18 | 16.8 | 21.9 | 23.4 | 22.9 | 27.3 |
| 2 hr | 30 | 25.2 | 33.1 | 34.6 | 34.8 | 39.9 |
| 3 hr | 40 | 31.7 | 41.3 | 42.9 | 42.7 | 49.0 |
| 4 hr | 52 | 37.2 | 47.8 | 49.4 | 49.5 | 56.5 |
| 6 hr | 60 | 46.6 | 57.9 | 59.3 | 59.8 | 67.4 |
| 8 hr | 70 | 54.1 | 65.6 | 66.7 | 66.8 | 74.8 |
| 10 hr | 80 | 60.7 | 71.5 | 72.2 | 72.5 | 79.8 |
| 12 hr | 90 | 66.0 | 76.1 | 76.2 | 76.2 | 82.8 |

For lipid and fatty acid based matrix tablet formulations, Compritol 888 was used as a lipid matrix. Details of the release profile obtained from in-vitro testing are shown in Table 4 below.

TABLE 4

Release Profiles for ER Torsemide using HPC.

| S. No. | Ingredients | B. No. 11-173-02 | B. No. 11-173-06 |
|---|---|---|---|
| 1 | Torsemide | 10 | 10 |
| 2 | Avicel PH 102 | 93 | — |
| 3 | Avicel PH 101 | — | 87 |
| 4 | Campritol 888 | 34 | 31 |
| 5 | Lactose Super Tab 30GR | 20 | 25 |
| 6 | PVP K 30 | 6 | 15 |
| 7 | Talc | 5 | 5 |
| 8 | Mag-Stearate | 2 | 2 |
|  | Tablet Weight | 170 | 175 |

Details of in-vitro dissolution testing results are shown in Table 5 below.

TABLE 5

In-Vitro Dissolution Testing Results

| Time in Hr | Target Release Profile | B. No. 11-173-02 | B. No. 11-173-06 |
| --- | --- | --- | --- |
| 1 hr | 18 | 16.2 | 17.3 |
| 2 hr | 30 | 25.3 | 27.2 |
| 3 hr | 40 | 33.9 | 35.6 |
| 4 hr | 52 | 43.3 | 43.5 |
| 6 hr | 60 | 60.1 | 56.1 |
| 8 hr | 70 | 70.9 | 65.2 |
| 10 hr | 80 | 78.6 | 72.4 |
| 12 hr | 90 | 84.6 | 77.7 |

Figure 3:
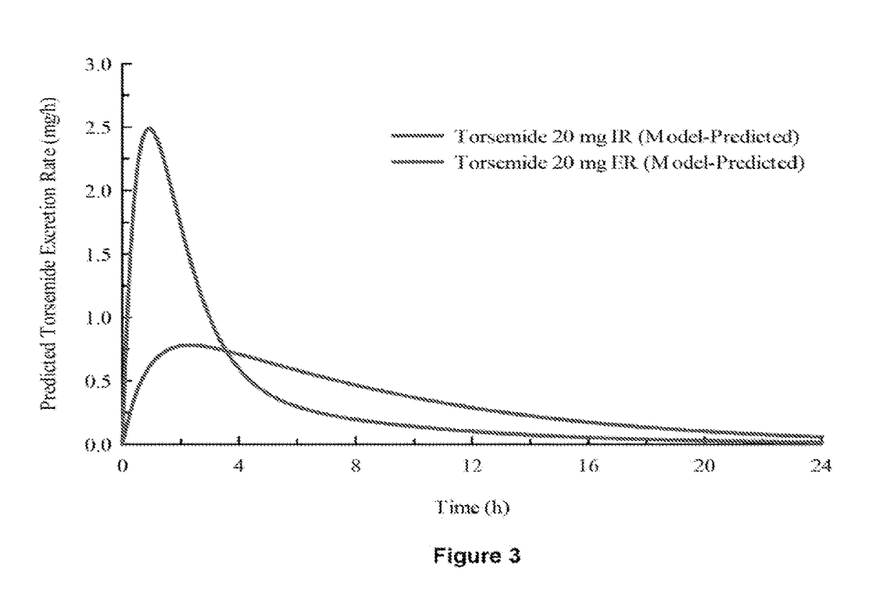
FIG. 3 shows model-predicted urinary Torsemide excretion rates after administration of 20 mg IR and ER formulations.
Figure 4:
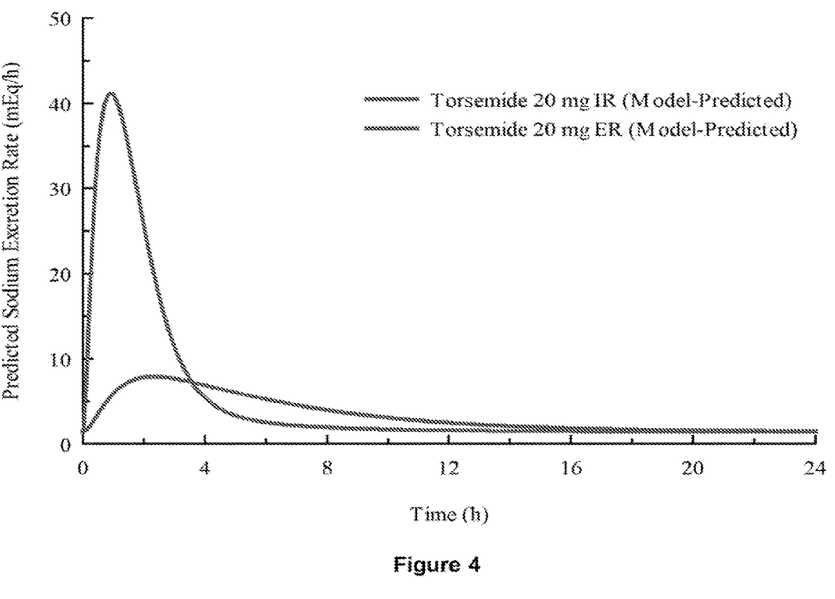
FIG. 4 shows model-predicted urinary sodium excretion rates after administration of 20 mg IR and ER formulations.
Figure 5:
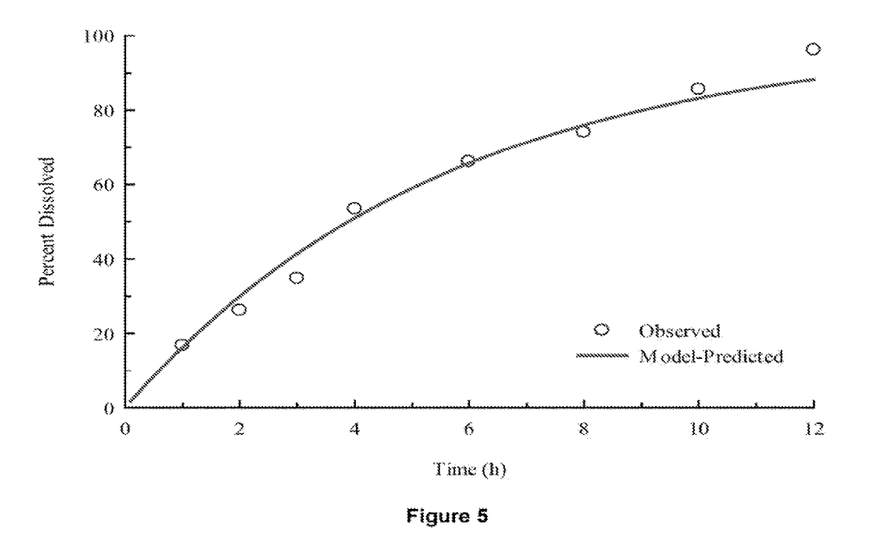
FIG. 5 shows observed and model-predicted percent dissolution of Torsemide from an ER oral dosage formulation.

Accordingly, the data listed in Tables 1-5 was used as a basis for the modeling curves shown in FIGS. 1-4 and part of FIG. 5.

FIG. 1 shows modeling of Torsemide plasma concentrations after administration of 20 mg IR and ER formulations. As can be seen, the ER formulation had a higher concentration of Torsemide 4 hours after administration than did the IR formulation.

Figure 2:
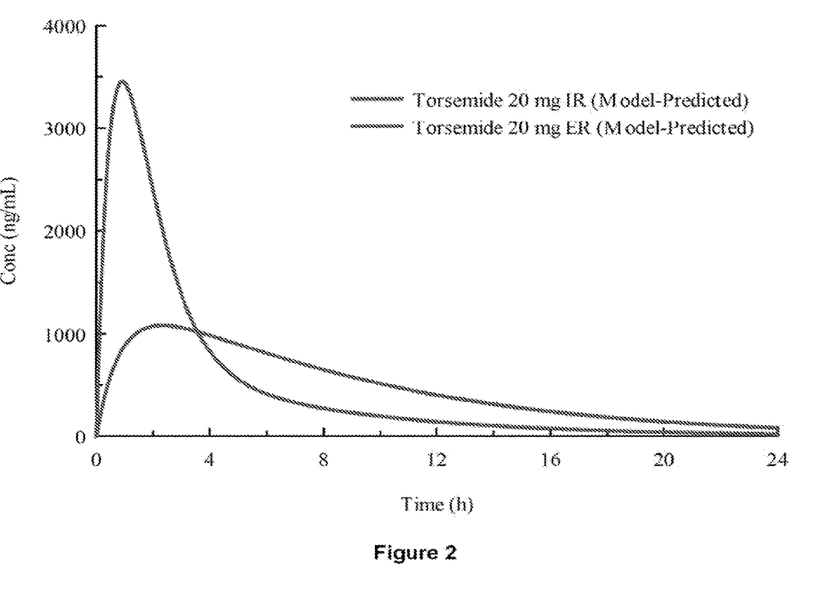
FIG. 2 shows model-predicted Torsemide plasma concentrations after administration of 20 mg IR and ER formulations.

FIG. 2 shows modeling of urinary Torsemide excretion rates of Torsemide after administration of 20 mg IR and ER formulations. As can be seen, much of the Torsemide of the IR formulation has been excreted within 4 hours of administration, whereas much less of the Torsemide of the ER formulation was excreted in the same time period.

FIG. 3 shows modeling of urinary Torsemide excretion rates of Torsemide after administration of 20 mg IR and ER formulations. As can be seen, much of the Torsemide of the IR formulation has been excreted within 4 hours of administration, whereas much less of the Torsemide of the ER formulation was excreted in the same time period.

FIG. 4 shows modeling of $Na^+$ excretion rates after administration of 20 mg IR and ER formulations. As can be seen, much of the $Na^+$ of the IR formulation has been excreted within 4 hours of administration, whereas much less of the $Na^+$ of the ER formulation was excreted in the same time period.

FIG. 5 shows observed and model-predicted percent dissolution of Torsemide from an ER oral dosage formulation. As can be seen, the model-predicted data closely matches that of the experimentally observed data.

Example 2

In-Vivo studies comparing Torsemide IR (Demadex Rx) with an extended-release (ER) formulation prepared by Sarfez, Inc.

Subjects:

Ten normal volunteers, aged 21 to 73 years were recruited. They had no significant past medical history, were not taking medications, and had normal values for blood urea nitrogen, serum creatinine, plasma electrolytes, liver function tests, hemogram, and urinalysis. All had a blood pressure less than 140/90 mmHg. Their body weights were 61.2 and 73.0 kg.

Trial Design:

Each subject received both of the Torsemide preparations in a randomized crossover design separated by a 3-week washout period. Subjects were pre-consented, admitted, and received a fixed constant diet for 3 days containing 300 mmol per day sodium and 45 mmol per day of potassium. This was verified by ashing and analyzing the food items fed to the subjects. Throughout the 3 days, subjects remained in the metabolic ward. Each meal was observed to ensure that subjects ate all the food given to them. Subjects remained within the facility for the duration of the study. No visitors were allowed. This provided strict control of food, sodium, and potassium intakes. Fluid was allowed ad libitum. During day 2, subjects collected a 24-hour urine. Thereafter, there was a 2-hour period during which the subjects were prepared for the procedures on the experimental day. They were weighed, an intravenous cannula inserted, and blood pressure and heart rate taken using an automated devices after 2 minutes of sitting. They were fasted for 12 hours prior to receiving the drug, and for 4 hours thereafter. To compensate for loss of salt intake (50 mmol of $Na^+$) during the breakfast period, they received 233 mL of 0.154 M saline solution immediately prior to drug administration. At zero time, they received 20 mg of Torsemide (IR or ER) with 300 mL of water. Immediately before ingestion, and for 23 hours thereafter, blood and urine samples were taken at designated times and another 24-hour urine was collected. After completion of the study, subjects were weighed, blood pressure and heart rate were recorded in the sitting position and they were discharged.

Analyses:

Urine samples were measured for volume and alliquots taken. $Na^+$ and $K^+$ concentrations were measured in an automated apparatus with an ion selective electrode, and creatinine concentrations in a creatinine analyser. Other alliquots were saved for measurement of Torsemide. A 35 ml blood sample was taken immediately prior to, and an 8 hour and 23 hours after the drug administration. This was analyzed for creatinine and for key hormones including plasma renin activity (PRA), serum aldosterone concentration (SAC), and brain natriuretic peptid (BNP).

Statistics:

Mean±sem data were calculated for each drug period in each individual subject. Within subject paired t-tests were used to assess differences in response to the IR versus DR preparations. A P value <0.05 were taken as statistically significant.

Figure 6:
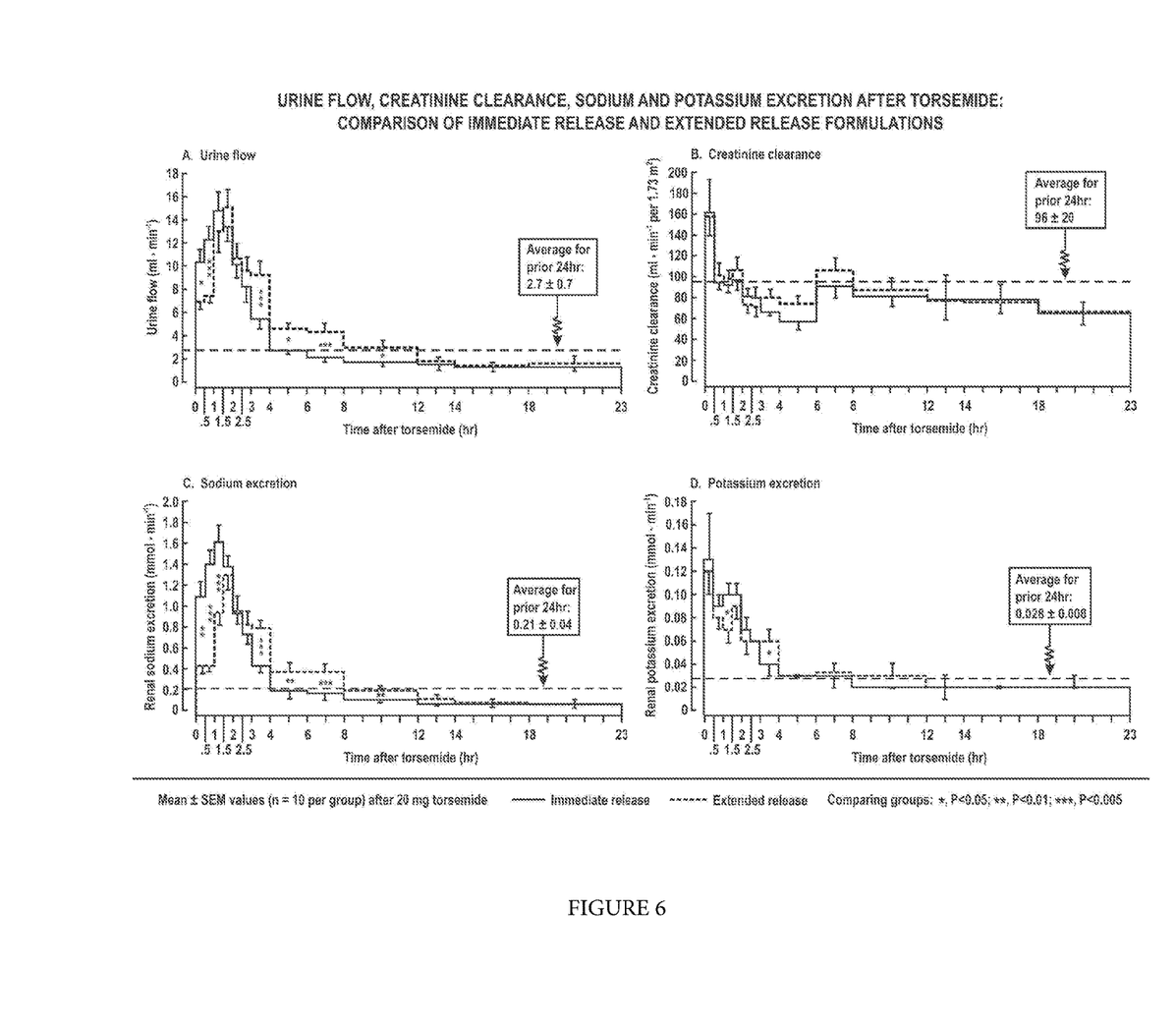
FIG. 6 shows Mean±SEM values (n=10 per group) for subjects receiving 20 mg of Torsemide as the IR preparation (continuous lines) or ER (dashed lines) as a function of time after Torsemide administration.

Results:

All 10 subjects completed both arms of the trial without any adverse effects. The patterns of urine flow, creatinine clearance, sodium and potassium excretion following drug administration are shown in FIG. 6. The average values for the prior 24-hours are indicated by horizontal dotted lines. Urine flow increased rapidly with the IR preparation and was significantly greater than ER for the first hour (FIG. 6A). Both preparations achieved a similar maximal urine flow rate of circa 15 mL·min$^{-1}$. By 3 hours, urine flow was significantly greater with ER than IR and remained so until 12 hours.

There was an initial sharp increase in creatinine clearance during the first ½ hr after administration of both formulations of Torsemide (FIG. 6B), but this returned abruptly to baseline and was reduced below baseline at 2 hours where it remained during most of the period from 2-23 hours. There were no significant differences in creatinine clearance between IR and ER during these periods.

Sodium excretion increased rapidly with the IR preparation to a maximum of 1*6 mmol per minute by 1.0 to 1.5 hr (FIG. 6C). Thereafter, rates of $Na^+$ excretion with the IR and ER preparation were similar until 3 hours when $Na^+$ excretion was greater with ER. This difference remained until 12 hours.

Potassium excretion increased sharply with both preparations and remained elevated for about 4 hr (FIG. 6D). $K^+$ excretion was greater with IR from 1-1.5 hours and with ER from 3-4 hours, but generally followed a similar pattern. After 12 hours, $K^+$ excretion was low in both groups.

The individual values for excretion and creatinine clearance for the 24-hour period immediately before and for 24-hour immediately after drug administration demonstrates that fluid excretion was not significantly changed after IR, but was increased significantly after ER resulting in a significantly 2.2-fold greater fluid loss of 906 mL after ER versus IR (data not shown). The creatinine clearance was significantly reduced by 25% following IR, but was not significantly changed following ER (data not shown).

Sodium excretion was increased significantly after both drugs, but the increased was significantly greater by 2.2-fold after ER (data not shown). Neither drug changed 24 hour potassium excretion.

Fluid excretion, Ccr, $Na^+$, $K^+$ excretion, FENa and FEK were not significantly different before administration of IR vs. ER (data not shown). A major difference between the responses to the two formulations is the greater loss of fluid and $Na^+$ after ER vs. IR. The GFR tended to fall after Torsemide (significant only for IR). The greater increased excretion of $Na^+$ after ER vs. IR was matched by a lesser reduction in GFR (and hence a better preserved filtered load of $Na^+$). The outcome was that there was a similar increase in fractional excretion of sodium (FENa) after IR and ER. Both formulations tended to increase $K^+$ excretion (not significant for either). The outcome of a rather higher $K^+$ excretion with a rather lower GFR (and hence a reduced filtered load of $K^+$) was a consistent increase in fractional excretion of potassium (FEK) that was similar for both formulations (data not shown).

The body weight, blood pressure, heart rate and plasma data (data not shown) demonstrates that body weight decreased significantly only after ER. The diastolic blood pressure was increased after IR, but tended to fall after ER, resulting in a significantly greater reduction in diastolic and mean blood pressures after ER compared to IR. Heart rate was reduced after both formulations. There were similar increases in serum creatinine but no significant changes in serum sodium or potassium concentrations.

The pharmokokinetic data are shown in Table 6. Compared to IR, the $C_{MAX}$ with ER was reduced 69% and the AUC was reduced 18-21%. The $T_{MAX}$ was prolonged 2.5-fold with a 59% reduction in AUC from 1 to 3 hours but a 97% increase in AUC from 8-10 hours. The Kel was reduced 32% resulting in a 45% increase in t½. The apparent $V_D$ was increased 79%. All of these differences were statistically significant.

TABLE 6

Pharmocokinetic Parameters after Administration of Torsemide: for Immediate Release and Delayed Release Formulations.

| Parameter | IR | DR | Fold difference | P value |
|---|---|---|---|---|
| $C_{MAX}$ (ng · ml$^{-1}$) | 2962 ± 412 | 905 ± 93 | −69 | <0.001 |
| AUC$_{0-t}$ (hr*/ng · ml$^{-1}$) | 6493 ± 688 | 5125 ± 552 | −21 | <0.001 |
| AUC$_{0-inf}$ (hr*/ng · ml$^{-1}$) | 6728 ± 704 | 5543 ± 565 | −18 | <0.001 |
| $T_{max}$ (hr) | 1.03 ± 0.13 | 3.53 ± 0.27 | +243 | <0.001 |
| AUC$_{1-3}$ (hr*/ng · ml$^{-1}$) | 2966 ± 294 | 1225 ± 161 | −59 | |
| AUC$_{8-10}$ (hr*/ng · ml$^{-1}$) | 203 ± 32 | 400 ± 50 | +97 | |
| Kel (hr) | 0.266 ± 0.03 | 0.194 ± 0.03 | −32 | |
| t$_{1/2}$ (hr) | 2.81 ± 0.25 | 4.07 ± 0.57 | +45 | |
| $V_D$ (ml) | 2498 ± 789 | 22414 ± 3139 | +79 | |

TABLE 6-continued

Pharmocokinetic Parameters after Administration of Torsemide: for Immediate Release and Delayed Release Formulations.

| Parameter | IR | DR | Fold difference | P value |
|---|---|---|---|---|

Mean ± Sem values
(n = 10 per group)

The main findings from this study are that a novel ER formulation of Torsemide that delivered the drug into solution over 12 hours led to a more prolonged period of natriuresis and diuresis and a two-fold larger loss of fluid and $Na^+$ than a traditional IR formulation. This resulted in a significant loss in body weight and a significantly greater reduction in diastolic and mean blood pressures. The $C_{cr}$ was reduced only after the IR preparation, which reduces the filtered load of $Na^+$. The combination of a greater loss of $Na^+$, but a better preserved filtered load of $Na^+$ after the ER compared to the IR formulation resulted in similar increases in FENa. For both drugs, a period of diuresis, natriuresis and kaliuresis was followed by sustained renal fluid and electrolyte retention. Neither drug led to a significant loss of potassium but again the lower levels of GFR reduced the filtered load of $K^+$ and led to significant, and similar, increases in FEK with both formulations. The ER formulation prolonged the time to maximal plasma Torsemide concentration by 2·5 fold with a corresponding reduction in Torsemide plasma levels 1 to 3 hours after dosing, but a doubling of plasma levels 8-10 hours after dosing. The overall bioavailability was reduced by 18%. The combination of an enhanced $Na^+$ loss despite a reduced bioavailability implies that the ER formulation had increased the diuretic efficiency.

The daily intake of $Na^+$ in this study of 300 mmol was designed to match prior studies in normal subjects given furosemide. The IR formulation of Torsemide (20 mg) did not increase fluid excretion or weight loss over 24 hours but led to a modest, but significant, $Na^+$ loss of 42 mmol.

Torsemide ER led to a similar maximal natriuresis as IR, but the peak was delayed by about 1 hour. The main effect of the ER preparation was to prolong the period of Na and fluid loss (relative to the IR) by 4 fold. This led to a significantly greater fluid and $Na^+$ loss with the ER formulation. These greater salt and water depleting actions of Torsemide ER were accompanied by significant reductions in body weight only after ER and by significantly greater reductions in diastolic and mean blood pressure after ER.

Therefore, the present findings that a ER formulation of Torsemide led to significantly more $Na^+$ and fluid loss than an IR preparation and that only the ER preparation increased fluid excretion and reduced body weight and diastolic blood pressure, carries clinical impact since these studies were conducted at a high level of salt intake. They raise the possibility that dietary salt restriction may not be absolutely required to achieve predictable salt and water loss and a reduction in blood pressure during treatment of patients with hypertension or CHF with ER Torsemide.

This study supports the hypothesis that a more prolonged duration of loop diuretic action enhances fluid and $Na^+$ loss. This study also confirms the hypothesis that a more prolonged duration of action of a loop diuretic would prolong the sojourn of plasma levels in the most efficient 25-70% of maximal range and in an improvement in overall natuiretic efficiency.

The regulation of GFR by loop diuretics is complicated and unresolved. Two factors have been identified that may increase the measured GFR. There is an artifactual initial increase caused by flushing out of concentrated GFR markers from the tubules by the abrupt increase in urine flow, as seen in the first 30 minutes of this study (FIG. 6B). Second, inhibition of tubuloglomerular feedback would reduce afferent arterolar resistance and should increase the GFR. Three factors have been identified that may reduce the GFR. Inhibition of fluid reabsorption raises the intertubular pressure substantially, which will limit the force for glomerular filtration. Second, the release of vasoactive agents could reduce the renal blood flow. Third, depletion of body fluid can cause renal vasoconstriction. The present study demonstrated that, after the early (artifactual) increase in GFR, there was a rapid return to baseline and below resulting in a significant 25% reduction in creatinine clearance in the 24 hours after Torsemide IR.

This constitutes a serious adverse effect since even modest reductions in GFR, especially when accompanied by release of vasoactive hormones, increases the risk of CVD and limit antihypertensive and fluid-depleting efficacy.

Thus, these results demonstrate that an ER formulation of Torsemide increased fluid and $Na^+$ loss and mitigated significant reductions in GFR, compared to the IR formulation. Thus, a method of mitigating the reduction in GFR and/or the increase in GFR may comprise administration of a therapeutically effective amount of the Torsemide ER formulations described herein to a patient in need thereof. Also, a method of increasing fluid and/or $Na^+$ loss may comprise administration of a therapeutically effective amount of the Torsemide ER formulations described herein to a patient in need thereof.

It has also been surprisingly found that the Torsemide ER formulations described herein, when administered, lead to a novel mechanism for Torsemide action in diuresis. It is known that torsemide acts on $Na^+/K^+/2Cl^-$ co-transporter in the kidney. It has been found that Torsemide also interacts with guanylate cyclase (GC), specifically membrane bound GC (mGC) and modulated actions of peptide hormones such as brain natriuretic peptide (BNP) and atrial natriuretic peptide. Structurally, torsemide is similar to atrial natriuretic peptide (ANP) and can compete for binding to its receptor. However, other members of the loop diuretic class such as furosemide cannot compete with ANP for binding to its receptor due to structural differences. Torsemide mediated modulation of GC, specifically mGC induces changes in cGMP and cGMP mediated pathways.

In the drawings and specification, there have been disclosed typical preferred embodiments of the invention and, although specific terms are employed, they are used in a generic and descriptive sense only and not for purposes of limitation, the scope of the invention being set forth in the following claims.

I claim:

1. An extended-release oral dosage formulation manufactured by wet granulation comprising: torsemide or a pharmaceutically acceptable salt thereof as an active ingredient; 27 wt % to 34 wt % of hydroxypropyl methyl cellulose; 25 wt % to 53 wt % of high density microcrystalline cellulose of nominal particle size of about 100 micrometer; and 6.5 wt % to 8 wt % of lactose monohydrate.

2. An extended-release oral dosage formulation manufactured by wet granulation comprising: torsemide or a pharmaceutically acceptable salt thereof as an active ingredient; 27 wt % to 34 wt % of hydroxypropyl methyl cellulose; 25 wt % to 53 wt % of high density microcrystalline cellulose of nominal particle size of about 100 micrometer; and 5 wt % to 8 wt % of lactose monohydrate.

3. The extended-release oral dosage formulation of claim 2, wherein said dosage formulation when administered orally to a subject, Cmax decreases by 60.87% wt-75.94% wt of a corresponding (by API weight) immediate release dosage form.

4. The extended-release oral dosage formulation of claim 2, wherein said dosage formulation when administered orally to a subject, Tmax increases by 281%-422% compared to that of a corresponding (by API weight) immediate release dosage form.

5. The extended-release oral dosage formulation of claim 2, wherein said dosage formulation when administered orally to a subject decreases AUC1-3 (1-3 hours after drug administration and measured as hr/ng·ml-1) between 48%-67% and increases AUC8-10 (8-10 hours after drug administration and measured as hr/ng·ml-1) between 149%-263% compared to that of a corresponding (by API weight) immediate release dosage form.

6. The extended-release oral dosage formulation of claim 2, wherein said dosage formulation when administered orally to a subject increases T½ between 32%-55% compared to that of a corresponding (by API weight) immediate release dosage form.

7. An extended-release oral dosage formulation manufactured by wet granulation comprising torsemide or a pharmaceutically acceptable salt thereof, 27 wt % to 34 wt % of hydroxypropyl methyl cellulose; 25 wt % to 53 wt % of high density microcrystalline cellulose of nominal particle size about 100 micrometer, 5 wt % to 8 wt % of lactose monohydrate, an aldosterone receptor antagonist or a pharmaceutically acceptable salt thereof, wherein said torsemide and said aldosterone receptor antagonist are comprised in an extended release dosage formulation.

8. A method of producing wet granules of an extended-release oral dosage formulation comprising the steps of mixing torsemide with 27 wt % to 34 wt % of hydroxypropyl methyl cellulose; 25 wt % to 53 wt % of high density microcrystalline cellulose; and 5 wt % to 8 wt % of lactose monohydrate by final weight of the granules.

9. A method of producing wet granules of an extended-release oral dosage formulation comprising the steps of mixing torsemide with 32-34 wt % of hydroxypropyl methyl cellulose; 25 wt % to 53 wt % of high density microcrystalline cellulose; and 5 wt % to 8 wt % of lactose monohydrate by final weight of the granules.

* * * * *